United States Patent [19]

Day

[11] Patent Number: 4,804,486

[45] Date of Patent: Feb. 14, 1989

[54] NAIL POLISH REMOVER

[75] Inventor: Betty L. Day, Grayslake, Ill.

[73] Assignee: Royal Care Beauty Products International, Inc., Chicago, Ill.

[21] Appl. No.: 169,493

[22] Filed: Mar. 17, 1988

[51] Int. Cl.$^4$ .......................... A61K 7/04; B08B 7/00; C23D 17/00; C11D 7/50

[52] U.S. Cl. ................................... 252/153; 252/171; 252/DIG. 8; 424/61; 134/38

[58] Field of Search ................. 252/153, 171, DIG. 8; 424/61; 134/38

[56] References Cited

U.S. PATENT DOCUMENTS 4,032,464  6/1977  Mausner .............................. 252/170
4,485,037  11/1984  Curtis .................................. 252/153

FOREIGN PATENT DOCUMENTS 1154347  9/1983  Canada.
6220720  6/1987  Japan.

OTHER PUBLICATIONS

Cosmetics: Science and Technology, 2d, ed., vol. 2, pp. 539–541, Mar., 1972.

*Primary Examiner*—Paul Lieberman
*Assistant Examiner*—Ronald A. Krasnow
*Attorney, Agent, or Firm*—Hill, Van Santen, Steadman & Simpson

[57] ABSTRACT

There is disclosed herein an improved cream-like nail polish remover consisting of a neutralizing-system and gelling-agent component, a solvent component, and an additive component. The component includes a gelling agent of an acrylic acid monomer and a neutralizing system N,N,N',N'-Tetrakis (2-hydroxypropyl) ethylenediamine and 2-ethyl-N-(2-ethylhexyl-1-hexamine. The solvent can be 2(3H)-furanone, dihydro-, which has a low vapor pressure at room temperature and a flash point above room temperature.

14 Claims, No Drawings

NAIL POLISH REMOVER

BACKGROUND OF THE INVENTION

This invention relates to a nail polish remover composition, and more particularly, to a composition for a cream-like consistency remover.

Commonly nail polish is an organic resin in a carrier liquid in which the resin is deposited on a finger-nail for decorative purposes.

For various reasons it may be desirable to remove the nail polish from the fingernail. Chemically nail polish is removed by applying a solvent, which may be in a carrier, to the polished nail for dissolving the resin therein for subsequent removal, as by wiping.

Present removers are generally a clear, free-flowing liquid which may include a water carrier and an acetone and/or ethylacetate solvent in appropriate proportions and various function-specific additives. This sysem presents a problem in that both acetone and ethylacetate have high vapor pressures at room temperature and low flash points. These properties make the removers volatile and inhibit use in a heated area, such as a kitchen or near a heat source.

Therefore, it is an object of this invention to provide a nail polish remover which does not exhibit a high vapor pressure and has a high flash point, preferably above room temperature.

Furthermore, present removers are a clear liquid, but it is believed that a cream-like consistency cosmetic-like material would be more esthetically and functionally desirable. This is particularly true if the remover employs a high flash point solvent.

It is therefore another object of this invention to provide a cream-like consistency and cosmetic-like nail polish remover material.

These and other objects of this invention will become apparent from the following disclosure and appended claims.

SUMMARY OF THE INVENTION

There is disclosed herein a nail polish remover composition which exhibits a cream-like consistency and includes a low vapor pressure and a high flash point solvent.

The remover includes a solvent identified as gamma-butyrolactone. This solvent exhibits a low vapor pressure and a high flash point. In order to achieve the cream-like consistency, the remover also includes a gelling agent and a neutralizing system in an amount effective to form the gel and neutralize the gel.

The gelling agent is an acrylic acid polymer sold under the trademark Carbopol by B. F. Goodrich in an amount effective to form a gel, usually about between 0.6 and 2.5 weight percent.

The neutralizing system is referred to commercially as Quadrol and as Di-2 ethylhexylamine is present in an amount effective to neutralize the gelling agent or between 2.0 and 7.5 weight percent. The neutralizing system is not usually a chelating agent, but in this system one of the components is a chelating agent, and the system is intended to neutralize the gelling agent or acrylic acid polymer and form a gel.

While gamma-butyrolactone is a preferred solvent, others can be used so long as the identified gelling agent and neutralizing system are used.

Additives such as antibacterial agents, perfumes, opacifiers, antioxidants, etc., are also used. Water is used to balance the composition to a 100 percent.

DESCRIPTION OF THE PREFERRED EMBODIMENT

1. General

The nail polish remover composition described hereinafter includes a number of components, only some of which are considered active in producing the remover. The principal components can be categorized as (a) the solvent; (b) the gelling agent and the neutralizing system; and (c) the additives and balancing agents.

2. The Preferred Solvent Component

The solvent used herein is commonly known as gamma-butyrolactone, is specifically identified in the CAS registry as 2(3H)-furanone, dihydro- and is identified by CAS Registry No. 000 000 96-48-0. The molecular formula is $C_4H_6O_2$ and is present in a weight percentage of about 86.00. This material is available from GAF Chemicals Corporation, 1361 Alps Road, Wayne, N.J. 07470. The material has a low vapor pressure, less than about 1 mm Hg at 20° C., and a flash point of about 200° F. For comparison, acetone's vapor pressure is about 180 mm Hg at 20° C. and has a flash point on the order of $-4$° F. In this composition gamma-butyrolactone preferably comprises about 80 percent by weight thereof. On a weight basis, a functionally permissible solvent weight range is between 77% and 94%.

Moreover, it is to be noted that there is an important relationship between the solvent and component and the gelling agent/neutralizer system component. The ratio of solvent-component to gelling agent/neutralizer system component is about 14/1 and the range of this ratio is 10/1 to 18/1.

While gamma-butyrolactone is the preferred solvent, other solvents with the similar characteristics can be used, such as 1-methyl-2-pyrolidione and di-propylene glycol.

3. Gelling Agent and Neutralizing System (a) The gelling agent is compatible with the solvent to form a gel or emulsion in the composition and provides cream-like consistency, minimizes component separation and extends shelf life. The gelling agent is an acrylic acid monomer having active carboxyl groups. These materials are sold under the trademark Carbopol by B. F. Goodrich Speciality Polymers and Chemicals Division, 6100 Oak Tree Boulevard, Cleveland, Ohio 44131, others are available. Within the Carbopol group, Carbopol 940 (an acrylic acid polymer referred to as Carbomer and with CAS No. 9007-17-4) is preferred and Carbopol 934 (CAS No. 977056-22-6) and Carbopol 941 may also be used. Carbopol 940 and 934 are polymers identified as having a molecular weight of about 3,000,000 and 940 has a molecular weight of about 4,000,000. Carbopol 940 is clear and 934 is slightly opaque.

In the composition, weight percentage is about 1.3 for 940 and 0.13 for 934 for a total of 1.43 percent. The acceptable range for the total gelling agent is between about 0.6 and 2.5 percent by weight.

(b) The neutralizing system is to neutralize the gelling agent so as to form a gel. One part of the neutralizing system is identified as N,N,N',N'-Tetrakis (2-hydroxypropyl) ethylenediamine, (CAS No. 102-60-3) sold under the trademark Quadrol by BASF Wyandotte Corp. In the system, Quadrol constitutes 2.2 percent by weight of the composition with a permissible range of between 1.8 and about 4.4 weight percent.

A second part of the neutralizing system is 2-ethyl-N-(2 ethylhexyl)-1-hexamine (CAS No. 106-20-7), sometimes referred to as Di-2 ethylhexylamine and sold by BASF Wyandotte Corp. Di-2 ethylhexylamine represents 2.2 weight percent of the composition and can be used in the range between 1.8 and 4.4 weight percent.

(c) The relationship between the gelling agent/neutralizing system is defined by the weight ratio 4.4/1.43 with the permissible weight ratio range being 1/1 to 4/1.

(d) The total gelling agent and neutralizing system weight percentage is 5.83 and range is between 2.4 and 7.5 weight percent.

(e) The relationship of the solvent component to the neutralizing system and gelling component is important. The weight ratio is about 14/1 and the permissible ranges are 10/1 to 18/1.

Use of this system assures a cream-like consistency for the product, that is, a viscosity of greater than about 800 centistokes.

3. Additional Components (a) An important additive is an antibacterial agent. For this purpose, Methylparaben (CAS No. 99-76-3) and Propylparaben (CAS No. 94-13-3) are used. They are present in the amounts of 0.20 weight percent and 0.10 weight percent, respectively. This additive is used in an amount effective to act as an antibacterial agent and acceptable total weight range is 0.15 to 0.30 weight percent.

Other acceptable and compatible antibacterial agents can be used.

(b) Aloe gel can be used as desired for cosmetic purposes. It is identified by CAS No. 977058-64-2.

(c) Perfumes and the like are also used. Here Tween-80 (CAS No. 9005-65-6) and any perfume is used. They are present in 0.10 and 0.03 weight percent. Tween-80 is used as a solubilizer and in this particular composition the ratio is 3 to 4 parts Tween to one part perfume.

(d) Opacifiers are also used. One such opacifier is a styrene acrylic emulsion commonly known as Lytron 621 and sold by Morton Thiokol, Inc., 333 West Wacker Drive, Chicago, Ill. 60606. In the instant composition, this is present in a weight amount of 0.8 weight percent and permissible ranges are between 0.2 and 2.

(e) An anti-yellowing agent is used such as ascorbic acid and sold by Pfizer Inc. Here this is present in, 0.1 weight percent or in the range of 0.1 to 1.0.

(f) Water makes up the balance of the composition to bring it to 100 percent by weight.

4. The Composition

One particularly suitable composition is identified below:

| Ingredient | CAS No. | %/Weight |
|---|---|---|
| Water | 7732-18-5 | 5.74 |
| Gamma-Butyrolactone | 96-48-0 | 86.0 |
| Quadrol | 102-60-3 | 2.2 |
| Di-2 Ethylhexylamine | 106-20-7 | 2.2 |
| Carbopol 940 | 9007-17-4 | 1.3 |
| Carbopol 934 | 977056-22-6 | 0.13 |
| Methylparaben | 99-76-3 | 0.20 |
| Propylparaben | 94-13-3 | 0.10 |
| Aloe Gel | 977058-64-2 | 1.00 |
| Tween 80 | 9005-65-6 | 0.10 |
| Perfume | | 0.03 |
| Lytron (40%) | | 0.8 |
| Ascorbic Acid | | .1 |

Although the table represents a preferred composition, other compositions within the preferred ranges set out above can be used.

5. Conclusion

As seen above, certain components are essential to a successful cream-like nail polish remover.

For example, the selection of a proper neutralizing system/gelling agent component is critical. Furthermore, their relationship to each other and to the solvent is important.

The preferred solvent is gamma-butyrolactone although others can be used.

Various additives are needed in effective amounts but are not critical.

Although this invention has been described with respect to preferred embodiments, it is not to be so limited as changes and modifications can be made which are within the full intended scope of the invention as defined by the appended claims.

I claim as my Invention:

1. A cream-like nail polish remover composition consisting of:
   a solvent in an amount effective to remove nail polish from a nail;
   a gelling agent in an amount effective to provide a cream-like consistency;
   a neutralizing system in an amount effective to cooperate with said gelling agent to render the composition essentially cream-like with a viscosity greater than about 800 centistokes and being a mixture of N,N,N',N'-tetrakis (2-hydroxy propyl) ethylene diamine and z-ethyl-N-(2-ethyl hexyl)-1-hexamine in the amount of between 1.8 and 4.4. weight percent;
   an antibacterial agent in an amount effective to inhibit bacterial growth; and
   water in an amount effective to balance the other ingredients and minimize the requirements for said other ingredients and permit the functioning thereof.

2. The composition of claim 1, wherein: the gelling agent is an acrylic acid polymer.

3. The composition of claim 2, wherein the gelling agent comprises between 0.6 and 2.5 weight percent of the composition.

4. The composition of claim 3, wherein the ratio of gelling agent to neutralizing system is between about 1/1 to 4/1.

5. The composition of claim 1, wherein the solvent is characterized by a vapor pressure of about 1 mm Hg at about room temperature and a flash point above room temperature.

6. The composition of claim 5, wherein the solvent is dihydro-2(3H)-furanone.

7. The composition of claim 6, wherein the ratios of solvent to gelling-agent/neutralizing-system is between about 10/1 and 18/1.

8. The composition of claim 7, wherein the ratio is about 14/1.

9. The composition of claim 6, wherein the solvent is between about 77 and 94 weight percent.

10. The composition of claim 9, wherein the solvent is present in an amount of about 86 percent by weight.

11. The composition of claim 1, further including:
aloe gel;
an odorant;
an opacifier; and
an anti-yellowing agent,
each present in an amount effective to achieve its function.

12. The composition of claim 11, wherein:
the antibacterial agent is a mixture of methylparaben and propylparabin;
the odorant is a mixture of a solubelizer and a perfume; and
the anti-yellowing agent is ascorbic acid.

13. A cream-like nail polish remover composition consisting essentially of:
gamma-butyrolactone in the amount of 7.7 to 94 weight percent;
an acrylic polymer gelling agent consisting of between 0.6 and 2.5 weight percent;
a neutralizing system of mixture of N,N,N',N'-Tetrakis (2-hydroxypropyl) ethylenediamine and 2-ethyl-N-(2 ethylhexyl)-1-hexamine in the amount of between 1.8 and 4.4 weight percent;
an antibacterial agent consisting essentially of a mixture of methylparaben and propylparaben in an amount between 0.15 and 0.30 weight percent;
aloe gel in the preselected amount to be effective for cosmetic purposes;
an odorant comprising a mixture of a solubilizer and perfume in an amount between 0.10 and 0.30 weight percent;
an opacifying agent in an amount of 0.2 to 2.0 weight percent;
an anti-yellowing agent of ascorbic acid in an amount between 0.1 and 1.0 weight percent; and
water in an amount effective to bring the total combination of all components to 100 percent by weight.

14. A composition as in claim 13, wherein:
said solvent is present in the amount of about 86 percent by weight;
said gelling agent is present in an amount of about 1.43 percent by weight;
said neutralizing system is present in an amount of about 4.4 percent by weight;
said antibacterial agent is present in an amount of about 0.3 percent by weight;
said aloe gel is present in an amount of about 1 percent by weight;
said odorant is present in the amount of about 0.13 percent by weight;
said opacifying agent is present in the amount of 0.8 percent by weight; and
said ascorbic acid is present in an amount of 0.1 percent by weight.

* * * * *